United States Patent [19]

Kao et al.

[11] 4,374,255

[45] Feb. 15, 1983

[54] PROCESS FOR PRODUCING SUBSTITUTED PYRROLES

[75] Inventors: James T. F. Kao; Robert E. Farritor, both of Baton Rouge, La.

[73] Assignee: Ethyl Corporation, Richmond, Va.

[21] Appl. No.: 239,431

[22] Filed: Mar. 2, 1981

Related U.S. Application Data

[63] Continuation-in-part of Ser. No. 137,249, Apr. 4, 1980, abandoned.

[51] Int. Cl.³ .......................................... C07D 207/337
[52] U.S. Cl. ..................................................... 548/531
[58] Field of Search .................................... 260/326.46

[56] References Cited

U.S. PATENT DOCUMENTS

| | | | |
|---|---|---|---|
| 3,752,826 | 8/1973 | Carson | 424/274 |
| 3,865,840 | 2/1975 | Carson | 260/326.46 |
| 3,952,012 | 4/1976 | Carson | 260/326.46 |
| 4,048,191 | 9/1977 | Carson | 260/326.46 |

OTHER PUBLICATIONS

Carson et al., J. Med. Chem., vol. 16, pp. 172–174, (1973).
Hantzsch; *Berichte der Deutschen Chemischen Gesellschaft*, pp. 1474–1479, (1890).
Fischer et al.; *Die Chemie des Pyrroles,* pp. 5–6, 233–234, (1943).
Grob et al.; Helv. Chim. Acta.; vol. 36; pp. 49–58, (1953).
Jones et al.; *The Chem. of Pyrroles,* p. 59, (1977).

*Primary Examiner*—Mary C. Lee
*Attorney, Agent, or Firm*—Donald L. Johnson; John F. Sieberth; James M. Pelton

[57] ABSTRACT

A process for the preparation of alkyl 1,4-dimethyl-3-ethoxycarbonylpyrrole-2-acetate compounds by reacting in a solvent in diloweralkyl acetone dicarboxylate, a chloromethyl lower alkyl ketone and an aqueous loweralkylamine in the presence of solids formation inhibiting amount of a lower alkanol having from 1 to about 6 carbon atoms.

7 Claims, No Drawings

PROCESS FOR PRODUCING SUBSTITUTED PYRROLES

CROSS REFERENCE TO RELATED APPLICATION

This application is a continuation-in-part of Application Ser. No. 137,249, filed Apr. 4, 1980, now abandoned.

BACKGROUND OF THE INVENTION

This invention relates to a process for producing substituted pyrroles, especially pyrrole-2-acetic acids and derivative compounds thereof. More particularly, the process of this invention is concerned with processes which produce 1,4-diloweralkyl-3-loweralkoxycarbonyl-pyrrole-2-acetate which is a useful intermediate for analgesic and anti-inflammatory pharmaceutical compounds.

It has been found difficult in the past to substitute pyrrole rings, which already contain substituents at other positions on the ring, at the 4-position because of steric hindrance and ring deactivation. Thus, Carson, U.S. Pat. No. 3,752,826 and U.S. Pat. No. 3,865,840, teach the preparation of certain 4-substituted 5-aroyl-pyrrole alkanoic acids and the corresponding salts, esters, nitriles, amides and substituted amides thereof represented by the formulas:

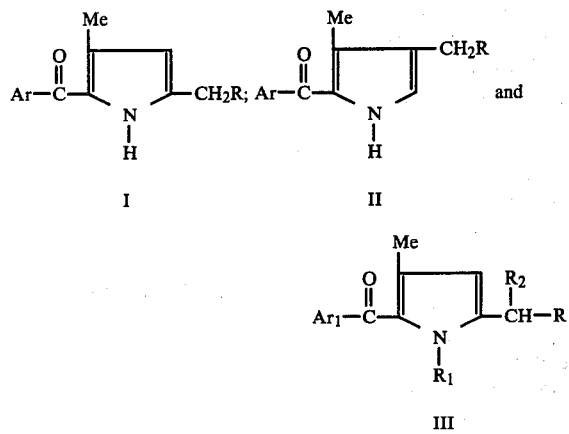

wherein:

Ar represents a member selected from the group consisting of phenyl, monosubstituted phenyl and polysubstituted phenyl, each substituent of said substituted phenyls being a member selected from the group consisting of halo, lower alkyl and lower alkoxy;

$Ar_1$ represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano, and methylthio;

R represents a member selected from the group consisting of COOH, COO-(lower alkyl), $CONH_2$, CONH-(lower alkyl) and CON-(lower alkyl)$_2$;

$R_1$ represents lower alkyl;

$R_2$ represents a member selected from the group consisting of hydrogen and lower alkyl, provided that when said Ar, is a member of the group consisting of nitrosubstituted phenyl, then, with regard to Formula III, $R_2$ is hydrogen;

Me is methyl;

and the non-toxic, therapeutically acceptable salts of such acids, such as are obtained from the appropriate organic and inorganic bases. According to Carson, supra, the 4-substituted 5-aroyl-pyrrole alkanoic acids must be obtained by condensation of the appropriate 1-aryl-1,2,3-butanetrione-2-oxime and an appropriate dialkyl acetonedicarboxylate as starting materials to provide the corresponding ring closed pyrrole, alkyl 5-aroyl-3-alkoxy carbonyl-4-methylpyrrole-2-acetate; or by condensation of an appropriate chloromethyl lower alkyl ketone added to a mixture of an appropriate di-loweralkyl acetonedicarboxylate, preferably the diethyl ester and a loweralkyl amine to provide the ring-closed pyrrole, alkyl 1,4-diloweralkyl-3-alkoxy-carbonyl pyrrole-2-acetate. These pyrrole intermediates are then treated as disclosed in U.S. Pat. Nos. 3,752,826 and 3,865,840 to obtain the desired 5-aroyl-4-lower alkyl-pyrrole-2-alkanoic acids and acid derivatives thereof useful as anti-inflammatory agents.

The condensation of chloromethylketone, ammonia and hydroxy crotonic acid alkylester through an anti-crotonic acid ester is taught by Fischer and Orth, *Die Chemie Des Pyrroles*, pp. 5–6 and 233–234, Edward Brothers, Inc., Ann Arbor, Mich., 1943. However, neither the 4-alkyl-substituent nor the diester functionality are disclosed in this reference.

Another pyrrole ring-closure synthesis, known as the Hantzsch pyrrole synthesis, teaches the interaction of alphachloro-aldehydes or ketones with beta-ketoesters and ammonia or amines to give pyrroles, Gowan and Wheeler, *Name Index of Organic Reactions*, p. 116, Longmans, Green and Co., Ltd., New York, N.Y., 1960.

In a similar manner, there is taught the reaction of chloroacetone with a salt produced from reaction of methyl amine and diethyl acetone dicarboxylate to give a 4-methylpyrrole, Jones and Bean, *The Chemistry of Pyrroles*, p. 59, 104, Academic Press Inc., New York, 1977. Also, the pyrrole synthesis from chloromethyl ketones and beta-ketocarboxylic esters with ammonia or amines is known, Krauch and Kunz, *Organic Name Reactions*, p. 211, John Wiley and Sons, Inc., New York, 1964. However, such teachings either fail to suggest the possibility of the pyrrole diester compounds or teach no more than Carson, supra, and are based thereon.

Specifically pertinent to the improved process of this invention, U.S. Pat. Nos. 3,752,826 and 3,865,840 teach that after reaction of, for example, aqueous methylamine with diethyl acetone-dicarboxylate and then adding chloroacetone at a temperature just below 60° C. for a period of two hours, the resultant reaction mixture is poured into ice-hydrochloric acid. The acidification acts to dehydrate the intermediate dihydroxy pyrrolidine to the desired pyrrole. However, the reaction forms solid intermediates which are difficult to agitate and conversion of the intermediate to the desired product results in an exothermic reaction which is difficult to control on a large scale. In an attempt to overcome the solids formation problem the reaction of diethyl acetone dicarboxylate with chloroacetone and aqueous methylamine was carried out in the presence of an added co-solvent, e.g., a halogenated hydrocarbon, such as methylene chloride, or an aromatic hydrocarbyl compound, such as toluene, at temperatures from 25° to 40° C. by Messrs. Dagani and Kao, respectively, as described in patent applications Ser. Nos. 137,231 and 137,250 now pending, filed on Apr. 4, 1980. Accordingly, the reaction could be improved to control the formation of solids and moderate the exothermic reaction.

THE INVENTION

In a search for improved processes for the reaction of a loweralkyl amine in aqueous solution with a diloweralkyl acetone dicarboxylate, it was discovered that when conducting the reaction at even lower temperatures, say from 0° to about 15° C., that even in the presence of an added co-solvent such as methylene chloride, solids formation with its attendant lower contacting and mixing problems will occur. It has, however, been discovered that the addition to the reaction mixture of a lower alkanol having from 1 to about 6 carbon atoms serves to aid the dissolution of solids formed in the reaction mixture at temperatures down to about 0° C. Accordingly, the present invention provides in a process for the preparation of a loweralkyl 1,4-diloweralkyl-3-loweralkoxycarbonyl-pyrrole-2-acetate of the formula:

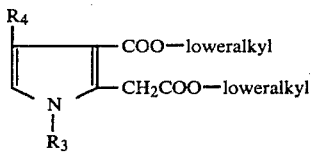

by reacting a chloromethyl loweralkyl ketone of the formula: Cl—CH$_2$—CO—R$_4$, with a diloweralkyl acetone dicarboxylate of the formula:

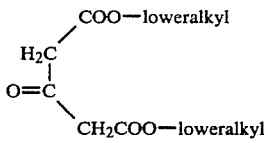

and an aqueous solution of a loweralkylamine of the formula: R$_3$NH$_2$, wherein the foregoing formulas said R$_3$ and said R$_4$ represent loweralkyl, the improvement comprising carrying out the reaction in the presence of a solids formation inhibiting amount of a lower alkanol having from 1 to about 6 carbon atoms.

As used in this invention, "loweralkyl" and "loweralkoxy" may be straight or branch chained saturated hydrocarbons having from 1 to 6 carbon atoms, such as, for example, methyl, ethyl, propyl, isobutyl, isopropyl, butyl, pentyl, hexyl and the like alkyls and, respectively, the corresponding alkoxys such as methoxy, ethoxy, propoxy, isopropoxy, and the like.

The loweralkoxy 1,4-diloweralkyl-3-loweralkoxycarbonyl-pyrrole-2-acetate of the present invention is preferably produced when the chloromethyl loweralkyl ketone is a chloroacetone. Chloroacetone is a readily available and relatively inexpensive ketone. The dicarboxylate is preferably dimethyl or diethyl acetone dicarboxylate which can be prepared according to known procedures. The other reactant is a loweralkylamine, preferably methylamine in order to have a 1-methylpyrrole compound produced. Should other 1-substituted pyrroles be desired, then other amines such as aryl amines or other alkyl amines, are also suitable reactants in the process of this invention. However, preferably, in order to produce the 1,4-diloweralkyl pyrrole compound, methylamine is used. Preferably, a 40% solution of methylamine is employed since this is conveniently available. More preferably, the solution is a 40% aqueous solution of methylamine.

As indicated hereinabove, it has been found that the use of an added amount of a lower alkanol has additional advantages. For one, the reaction can be carried out at lower temperature than heretofore practiced while obtaining comparable yields with prior art processes. Another advantage is that the inhibition of solids formation during the addition of methylamine allows more efficient agitation which is conducive to good reactant contact, better heat distribution, more effective process control and requires less power for agitation.

The alkanols useful in the present invention are those which have the ability to reduce or inhibit the formation of solids during the reaction. It has been found that such solids formation inhibiting alkanols are lower alkanols, such as those having from 1 to about 6 carbon atoms; for example, methanol, ethanol, propanol, isopropanol, butanol, sec-butanol, isobutanol, pentanol, hexanol and the like are suitably employed. Of course, substituted alkanols are within the scope of the present invention so long as the substituents are inert to the reactants and products of the reaction and do not adversely affect the power of the alkanol to dissolve the solids which would otherwise form. The preferred alkanol is ethanol. The alkanols are employed in amounts sufficient to inhibit the formation of solids during the first portion of the reaction. Because the useful alkanols have varying abilities to inhibit solids formation, it is to be expected that the alkanols are employed in varying amounts. Preferably, the lower alkanols useful in this invention are employed in a solids formation inhibiting amount which falls within the range of about 0.1 to about 18 moles of the alkanol per mole of the dilower alkyl acetone dicarboxylate. More preferably, the alkanol is employed within the range of about 0.5 to about 6 moles per mole of the dilower alkyl acetone dicarboxylate.

When desired, the co-solvent employed in the process of this invention is an inert, water-immiscible organic solvent with a high degree of solubility for the dialkyl acetone dicarboxylate and the cyclized, substituted pyrrole product. Additionally, the added co-solvent must be relatively water-immiscible and capable of extracting the loweralkylamine from the aqueous solution thereof for reaction in the organic phase.

It has been found that several types of organic solvents have utility in the present process. Typically, organic solvents which are aromatic hydrocarbon compounds, aliphatic hydrocarbon compounds, halogenated aromatic and aliphatic hydrocarbon compounds and the like which have boiling points from about 30° to about 200° C. at normal pressures are particularly suitable because such solvents in addition to preventing solids formation by solubilizing reactants and products also provide a method of convenient heat removal by operation at reflux. Specifically, chlorinated and brominated hydrocarbon solvents such as carbontetrachloride, carbontetrabromide, chloroform, bromoform, methylene chloride, methylene bromide, tetrachloroethane, ethylenedichloride, ethylene dibromide, chlorobenzene, bromobenzene, o-dichlorobenzene and the like are examples of useful solvents. Further, simple aromatic hydrocarbons, such as benzene, xylene and toluene are likewise useful and practical added co-solvents in the process of the present invention. Of particular preference, methylene chloride provides the combined properties of solubility, heat removal, water-immiscibility, sufficient inertness to the reactants and products and low cost for best results in the present process. Although methylene chloride is preferred, any solvent having similarly advantageous properties can be used. It is only necessary to maintain the diloweralkyl acetone dicarboxylate and the substituted pyrrole in solution while extracting the lower alkyl amine from aqueous solution to be usefully employed in the present process.

The reaction of, for example, diethyl acetone dicarboxylate, methylamine and chloroacetone is carried out by adding an aqueous solution of methylamine to a solution of the other reactants in, for example, methylene chloride. Although not preferred, the addition may also be carried out inversely, i.e., adding a solution of diethylacetone dicarboxylate and chloroacetone to a solution of aqueous methylamine. Temperatures can be kept in the range initially from about 0° C. up to about 15° C. The reaction is conducted for a period of time sufficient to complete the reaction and then the resultant solution is acidified or thermally cyclized to finish the product.

Although the most preferred and advantageous results occur with the process of this invention at reaction temperatures in the range of 0°–15° C., the reaction can be carried out at temperatures both higher and lower than the preferred range. At lower temperatures the reaction slows considerably, however, and is less practical. In contrast, at reaction temperatures greater than about 15° C., and up to about 35° C., there is less need for the additional dissolution effects of the added presence of the alkanol. Thus, as the reaction temperature increases the reaction mixture is more fluid and there is less tendency for the reaction products or intermediates to form separable solids. At the same time, it is not possible to say with certainty at what point the additional lower alkanol has lost its beneficial solids formation inhibiting purpose because not only the reaction temperature, but the nature of the lower alkanol, reaction solvent, reactants and other reaction conditions must be taken into account.

The process of the present invention can be illustrated, but not limited, more fully by the following Examples.

EXAMPLE 1

To a suitable reactor fitted with condensation/distillation head was added with agitation 411.8 grams of methylene chloride, 984.4 grams of a 20.52 weight percent solution of diethyl acetone dicarboxylate in methylene chloride, 23.4 grams of ethanol (as 2B-ethanol) and 128 grams of chloroacetone. The reactor contents were chilled to 5° C. and 620.5 grams of methylamine as a 40 weight percent aqueous solution was added over a period of about 1 minute. The temperature rose to 13.5° C. After addition of the methylamine there were very little solids formed at the top of the reactor and good agitation was observed. The temperature reached 24.6° C. while the brine bath remained at 2° C.

Then heating started on the brine bath and the reactor contents reached 37.8° C. and began refluxing for about 30 minutes. The brine bath was then heated to about 100° C. over a period of 2 hours and the reactor contents reached 90° C. The heating was then stopped and the condensate phases separated while hot. Analysis by VPC and NMR indicates a 64.69 percent yield of ethyl 1,4-dimethyl-3-ethoxycarbonylpyrrole-2-acetate.

In a similar manner, several other experiments were carried out varying the amount of ethanol and other reactants to study their effect on the yield of ethyl 1,4-dimethyl-3-ethoxycarbonylpyrrole-2-acetate with the results being given in the following table.

TABLE I

Preparation of Ethyl 1,4-Dimethyl-3-ethoxycarbonylpyrrole-2-acetate (PDE) by Reaction of Diethyl Acetone Dicarboxylate (ADC), Chloroacetone (CA) and Aqueous Methylamine (MA) in Methylene Chloride (MeCl$_2$) and Ethanol (EtOH)

| Example No. | EtOH | MeCl$_2$ | CA | MA | ADC | Percent Yield of PDE |
|---|---|---|---|---|---|---|
| 2 | 0 | 16.3 | 1.36 | 8.06 | 1 | 60.8 |
| 3 | 0 | 16.3 | 1.36 | 8.06 | 1 | 52.1, 54.6 |
| 4 | 0 | 16.3 | 1.36 | 8.06 | 1 | 65.2 |
| 5 | 0 | 16.3 | 1.36 | 8.06 | 1 | 52.7 |
| 6 | 5.52 | 16.2 | 1.36 | 8.06 | 1 | 51.1 |
| 7 | 0 | 16.3 | 1.36 | 8.06 | 1 | 51.9 |
| 8 | 1.5 | 14 | 1.38 | 8.0 | 1 | 55.8 |
| 9 | 6.0 | 22.2 | 1.38 | 8.0 | 1 | 55.2 |
| 10 | 14 | 14 | 1.38 | 8.0 | 1 | 38.2 |
| 11 | 18 | 10 | 1.38 | 8.0 | 1 | 39.6 |
| 12 | 1.4 | 12.6 | 1.11 | 6.7 | 1.2 | 58.9 |

It should be noted that when ethanol was employed in the above examples very few or no solids were observed. Moreover, other lower alkanols, as hereinabove described, can be used with similar results in the process of the present invention. Further, it is preferred that the alkyl groups on the dilower alkyl acetone dicarboxylate be the same as the alkyl portion of the lower alkanol added. This is because during the reaction it is believed that some transalkylation may occur leading to the formation of mixed pyrrole diesters. Although technically feasible, production of pyrrole diesters with mixed ester groups is impractical because of complications encountered in subsequent processing, recovery and recycle steps.

The Carson patents, U.S. Pat. Nos. 3,752,826 and 3,765,840, are hereby incorporated by reference as if fully set forth.

Having disclosed the process of the present invention, one skilled in the art can readily envision variations, modifications and changes within the scope and spirit of this invention. Therefore, it is desired that the present invention be limited only by the lawful scope of the following claims.

What is claimed is:

1. In a process for the preparation of a loweralkyl 1,4-diloweralkyl-3-loweralkoxycarbonyl-pyrrole-2-acetate of the formula:

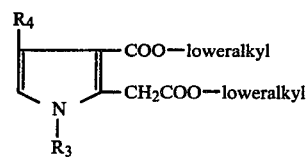

by reacting a chloromethyl loweralkyl ketone of the formula: Cl—CH$_2$—CO—R$_4$, with a diloweralkyl acetone dicarboxylate of the formula:

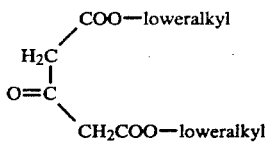

and an aqueous solution of a loweralkylamine of the formula: R₃NH₂, wherein the foregoing formulas said R₃ and said R₄ represent loweralkyl, the improvement comprising carrying out the reaction in the presence of a lower alkanol having from 1 to about 6 carbon atoms at a molar ratio of from about 0.1 to about 18 moles of said alkanol to each mole of said diloweralkyl acetone dicarboxylate.

2. The improved process of claim 1 further characterized by cooling the reactants initially to about 0° C.

3. The improved process of claim 1 wherein said alkanol is ethanol.

4. The improved process of claim 1 wherein said alkanol is ethanol and the molar ratio is 0.5 to about 6 moles ethanol to each mole of said diethyl acetone dicarboxylate.

5. The improved process of claim 1 wherein said reacting is carried out in the presence of a co-solvent which is an inert, water-immiscible organic solvent.

6. The improved process of claim 1 wherein said reacting is carried out in methylene chloride as a solvent.

7. The improved process of claim 6 further characterized in that said alkanol is ethanol.

* * * * *